United States Patent
Letendart et al.

(10) Patent No.: US 6,432,109 B1
(45) Date of Patent: Aug. 13, 2002

(54) CONNECTION DEVICE FOR OSTEOSYNTHESIS

(75) Inventors: Joël Letendart, Saint Saulve; Denis Cordonnier, Provin; Jean-François Desrousseaux, Haubourdin; Philippe Stahl, Sainghin en Melantois; Henri Mathevon, Dunkerque, all of (FR)

(73) Assignee: Societe de Genie Medical S.G.M., Saint Etienne (FR)

( * ) Notice: Subject to any disclaimer, the term of this patent is extended or adjusted under 35 U.S.C. 154(b) by 0 days.

(21) Appl. No.: 09/647,404

(22) PCT Filed: Mar. 30, 1999

(86) PCT No.: PCT/FR99/00742

§ 371 (c)(1),
(2), (4) Date: Feb. 5, 2001

(87) PCT Pub. No.: WO99/49802

PCT Pub. Date: Oct. 7, 1999

(30) Foreign Application Priority Data

Mar. 31, 1998 (FR) .............................................. 98 04257

(51) Int. Cl.[7] .............................................. A61B 17/70
(52) U.S. Cl. ...................................................... 606/61
(58) Field of Search ..................................... 606/61, 60

(56) References Cited

U.S. PATENT DOCUMENTS

| 5,084,048 | A |   | 1/1992  | Jacob et al. |
| 5,129,899 | A | * | 7/1992  | Small et al. .................. 606/61 |
| 5,312,404 | A |   | 5/1994  | Asher et al. |
| 5,395,371 | A | * | 3/1995  | Miller et al. .............. 606/61 X |
| 5,474,551 | A |   | 12/1995 | Finn et al. |
| 5,498,263 | A | * | 3/1996  | DiNello ..................... 606/61 X |
| 5,545,163 | A | * | 8/1996  | Miller et al. .............. 606/61 X |
| 5,613,968 | A |   | 3/1997  | Lin |
| 5,810,817 | A |   | 9/1998  | Roussouly et al. |

FOREIGN PATENT DOCUMENTS

| DE | 195 12 709 | 10/1996 |
| EP | 0 408 489  | 1/1991  |
| EP | 0 729 731  | 9/1996  |
| FR | 2 692 471  | 12/1993 |
| FR | 2 693 365  | 1/1994  |
| FR | 2 730 155  | 8/1996  |

* cited by examiner

*Primary Examiner*—Jeffrey A. Smith
(74) *Attorney, Agent, or Firm*—Wolf, Greenfield & Sacks, P.C.

(57) ABSTRACT

The ostheosynthesis connection device of the invention is designed to connect a screw for implanting in the spine to a vertebral support rod. The screw is constituted by a bottom first threaded portion, a head having flats and a curved base, and a top second threaded portion in line with the first. A nut having a curved base is suitable for co-operating with the second threaded portion. For connection with the screw, a connection piece has a hole of inside diameter that is greater than the outside diameter of the second threaded portion of the screw, and around said hole it has curved top and bottom bearing faces such that the connection piece is locked in position relative to the screw once the nut has been tightened by the curved base of the nut bearing against the top bearing face thereof and by the bottom bearing face being clamped against the curved base of the head of the screw.

9 Claims, 3 Drawing Sheets

CONNECTION DEVICE FOR OSTEOSYNTHESIS

The present invention relates to a connection device usable in surgical instrumentation of the spine. It relates more particularly to a device suitable for making the connection between screws for securing to a pedicle or to a joint, and a vertebral support rod that is to hold the vertebral column in a given alignment. The instrumentation comprising the screws, the connection device, and the vertebral support rod is used in particular for performing arthrodesis on a segment of the spine.

BACKGROUND OF THE INVENTION

Document EP 0 425 783 discloses such a connection device constituted by a one-sided clamp for fixing a pedicle screw to a vertebral support rod having respective central axes situated in different planes. It is important to be able to vary the inclination of both axes, i.e. both the axis of the vertebral support rod and the axis of each pedicle screw, and,similarly it is important to be able to match the distance between the two axes to the shape desired by the surgeon.

In document EP 0 425 783, freedom in angular inclination is given by means of a ball constituting either the head of the pedicle screw or one end of the connection piece. The ball must necessarily be inserted in a socket and locked in position in the socket once the angular inclination has been set. When the ball constitutes the head of the pedicle screw, the socket forms a part of the connection piece, and in the embodiments described in that prior document, it is constituted by recesses formed in two distinct parts of the connection piece, which parts are hinged to each other like jaws, with the ball being locked by moving the jaws towards each other. Thus, when the pedicle screw is put into place, it must necessarily be passed beforehand through the part of the connection piece which acts as the bottom jaw, before it is itself inserted into the bone. The presence of the connection piece while the pedicle screw is being implanted can be an impediment for the surgeon.

In the embodiment where the ball constitutes one end of the connection piece, the socket is constituted by a recessed portion of the head of the pedicle screw. In that case, while the pedicle screw is being implanted, it is important for the head of the screw to be oriented in substantially the appropriate direction for passing the vertebral support rod, and that constitutes a constraint on the surgeon.

Elsewhere, document DE 195 12 709 describes an ostheosynthesis device comprising a screw for implanting, a connection piece, and fixing means for fixing the connection piece to the screw for implanting. The fixing means are constituted by two elements, each having a convex hemispherical portion. The screw for implanting has a concave hemispherical base and two threaded portions, one for implanting in the bone and the other for assembly with the connection piece. The connection piece is fixed to the screw for implanting by clamping the connection piece between the two elements forming the fixing means. The convex portion of each of the elements co-operates with a respective concave portion: one with the concave base of the head of the screw for implanting; and the other with a nut which has a concave portion and which is screwed onto the threaded portion for assembling the screw for implanting with the connection piece.

Unlike the device described in document EP 0 425 783, the device of DE 195 12 709 enables the connection piece to be released from the screw, thereby making the device easier to install.

Furthermore, since the elements forming the means for fixing the connection piece to the device comprise hemispherical portions with a common center, it is easy to vary the angular orientations of the axes of the screw and of the support rod without taking special precautions while implanting the screw in the spine in order to ensure that the screw is already initially oriented in substantially the desired direction.

Nevertheless, using such a device increases the amount of handling that the surgeon needs to perform. After implanting the screw in the spine, the surgeon must position the elements forming the above-described fixing means correctly, thereby increasing the length of time required to install the device. Furthermore, the presence of those fixing meats increases the'size of the connection device and that is not desirable for the patient.

OBJECT AND SUMMARY OF THE INVENTION

The object the Applicant has set out to achieve is to propose a connection device which mitigates the drawbacks of the above-described devices.

It comprises an ostheosynthesis connection device for connecting a screw suitable for implanting in the spine to a vertebral support rod, the respective central axes thereof not lying in the same plane, the device comprising a connection piece, means for locking the vertebral support rod onto said connection piece, the screw for implanting being constituted by a bottom first threaded portion for implanting in the spine, a head having a curved base, and a top second threaded portion in line with the first threaded portion, the connection piece having, for connection with the screw, a hole of inside diameter greater than the outside diameter of the second threaded portion.

In characteristic manner, according to the invention, the head of the screw has flats, and the device also comprises a nut having a curved base and suitable for co-operating with the second threaded portion; the locking of the connection piece in position on the screw being obtained in characteristic manner, once the nut has been tightened, by the curved base of the nut bearing against the top bearing face of the connection piece, and by the bottom bearing face of the connection piece bearing against -the curved base of the head of the screw, the curved surfaces of the bases of the head of the screw, of the locking nut, and of the top and bottom bearing faces of the connection piece being portions of spheres all having their centers in the same position, one of the top and bottom bearing faces being convex, and the other being concave.

While the instrumentation is being put into place, the surgeon can implant all of the pedicle screws without constraint using a wrench on the flats, and without being concerned about the orientations of the screws. Each connection piece is put into place by inserting the top threaded rod through the hole having a curved seat, said threaded rod serving as a guide rod for putting said connection piece into place.

Since the top and bottom bearing surfaces of the connection piece are portions of concentric spheres, it is easy to adjust the angle between the screw and the vertebral support rod, and quasi-infinite angular variation in the respective positions of these two members is possible. Furthermore, the locking in position obtained in this way is particularly effective because the various members are held together, whatever their relative position, by pressing surface areas against one another.

In a preferred embodiment, the locking means for locking the connection piece on the vertebral support rod comprise:

a) a locking piece having a first passage for the vertebral support rod, a second passage for a portion of the connection piece, the first and second passages being substantially perpendicular and sharing a common inside volume in which the rod and the connection plate can come into contact, and a threaded third passage opening out into the inside volume of the first or second passage; and b) a set screw suitable for screw engagement in the third passage to lock the vertebral support rod and the connection plate in position by clamping the set screw, the rod, the plate, and the piece against one another.

The presence of the locking piece sliding on the connection piece makes it possible to adjust the spacing between the screw for implanting and the vertebral support rod.

In this configuration, the connection piece does not have a slot as in document EP 0 425 783. The portion of the connection piece which is designed to slide in the second passage of the locking piece can have any configuration: preferably, it is a plate of substantially rectangular section with rounded sides, the second passage being shaped to enable fitted sliding of the locking piece over the portion of the connection piece that goes beyond the curved seat faces. The rectangular shape of the section of this portion of the connection piece also makes it possible to reduce the size of the locking piece in comparison to a portion having the same strength but being of circular section.

Similarly, this configuration makes it possible to fix the connection piece on the screw for implanting and then once that operation has been performed, to adjust the spacing between the vertebral support rod and the screw for implanting without acting on the way in which the connection piece is fixed to the screw and thus without any risk of disconnecting them or changing their respective positions.

In document DE 195 12 709, the spacing between the screw and the vertebral support rod is adjusted simultaneously while fixing the connection piece on the screw by positioning the second threaded rod in the hole in the connection piece which has a diameter greater than the diameter of the second threaded rod.

Preferably, the first passage for the vertebral support rod is of oblong cross-section, thereby allowing the rod to move a little in the height direction prior to the set screw being tightened and enabling an already curved rod to be passed therethrough.

In a preferred embodiment, the locking piece is a cylindrical piece, the first and second passages extending along diametral directions that-are perpendicular to each other, and the third passage being formed in one of the two circular faces of the cylinder and opening out into the inside volume of the first passage.

Advantageously, the connection piece has an abutment-forming element or is shaped in such a manner as to be capable itself of constituting an abutment for the locking piece while it is free to slide, prior to the set screw being tightened.

Advantageously, the top second threaded portion of the screw is suitable for being broken off, presenting a zone of weakness. In this particular disposition, after the curved-base nut has been tightened to lock the pedicular screw in position relative to the connection piece, it is possible to remove the top portion of the second threaded portion of the pedicular screw that projects from the nut, thereby minimizing the overall size of the instrumentation.

BRIEF DESCRIPTION OF THE DRAWINGS

The present invention will be better understood on reading the following description of a preferred embodiment of the ostheosynthesis connection device for interconnecting a vertebral support rod and a screw that is suitable for implanting in the spine, as shown in the accompanying drawings, in which.

MORE DETAILED DESCRIPTION

Figure 1:
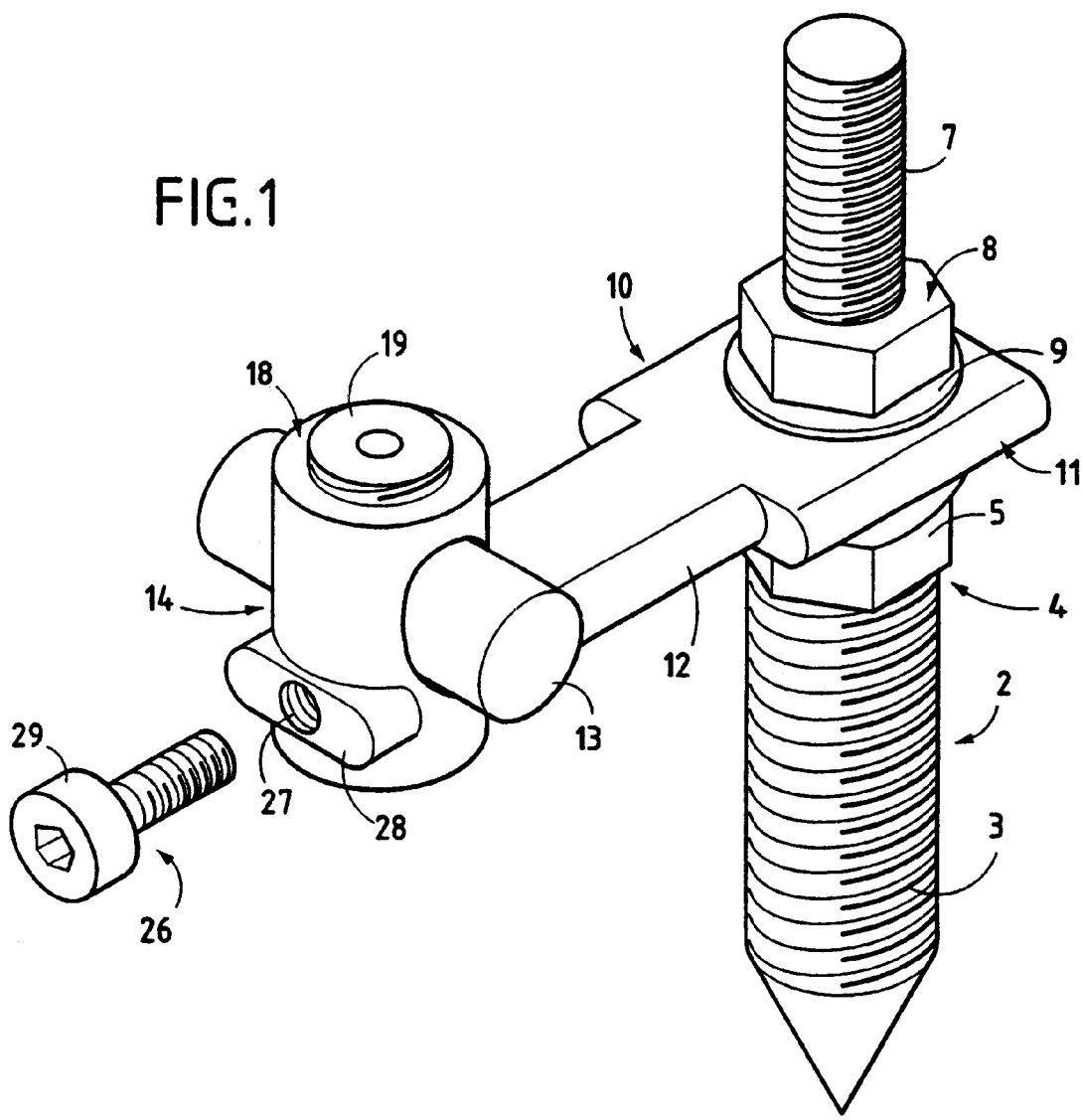
FIG. 1 is a diagrammatic perspective view of the connection device.

Arthrodesis is a surgical technique which consists in fusing together two bones of a diseased joint in order to prevent relative movement therebetween. In arthrodesis of the spine, this technique serves to fuse together two or more adjacent vertebrae. It requires said vertebrae to be fixed together in temporary, or even permanent manner by suitable surgical instrumentation. Conventionally, the instrumentation comprises screws for securing to a pedicle or to a joint, and a vertebral support rod which is generally a very stiff metal rod for holding the segment of spine in question in a determined configuration. The instrumentation also has connection means for locking the relative position between the pedicle screws and the vertebral support rod. Such instrumentation is known, in particular from document EP 0 425 783.

In the invention, the pedicle screw 2 presents a special structure having a first threaded portion 3 at its bottom surmounted by a head 4 with flats 5 and a curved flank or base 6, and then by a second threaded portion 7 at its top in line with the first threaded portion 3 at its bottom, with the head 4 being a hexagonal head, for example.

A nut 8 having a curved base 9 is suitable for screw engagement on the second threaded portion 7 at the top of the pedicle screw 2. It can be embodied, for example, by a hexagonal nut co-operating with a threaded rod 7 having a diameter of about 5 mm.

Figure 3:
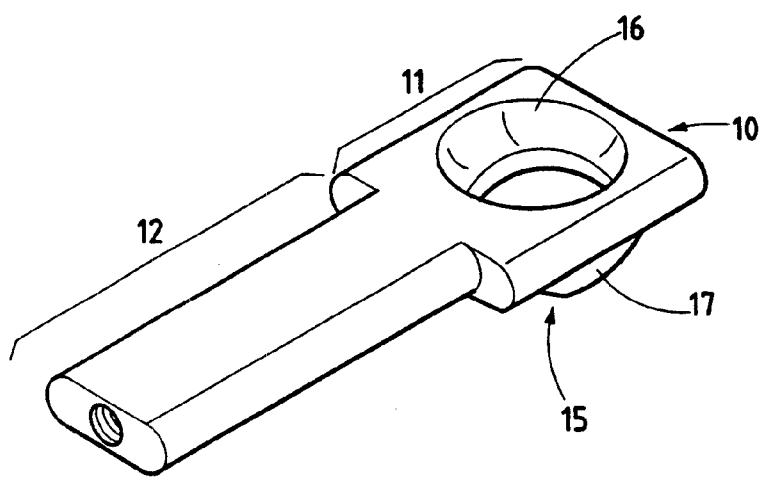
FIG. 3 is a diagrammatic perspective view of the connection plate.
Figure 2:
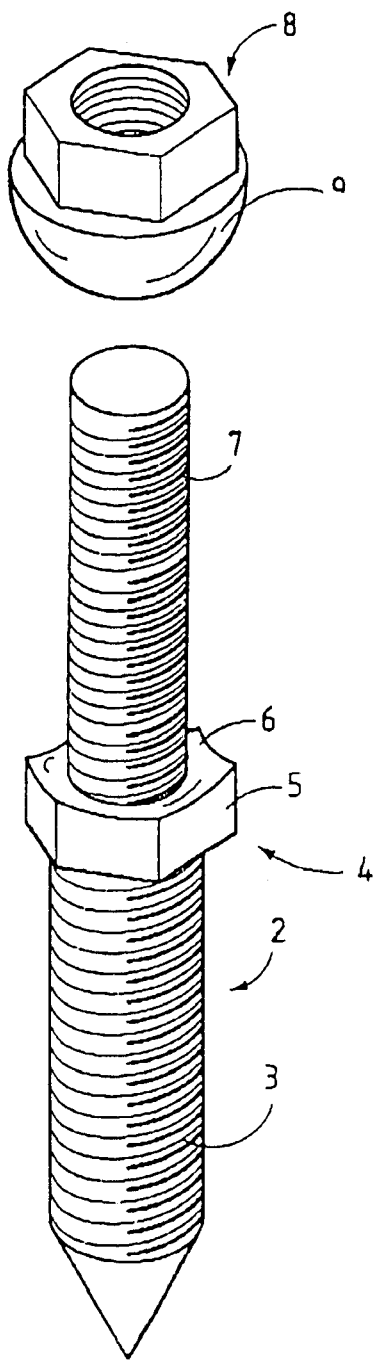
FIG. 2 is a diagrammatic perspective view of the pedicle screw and the curved-base nut.
Figure 4:
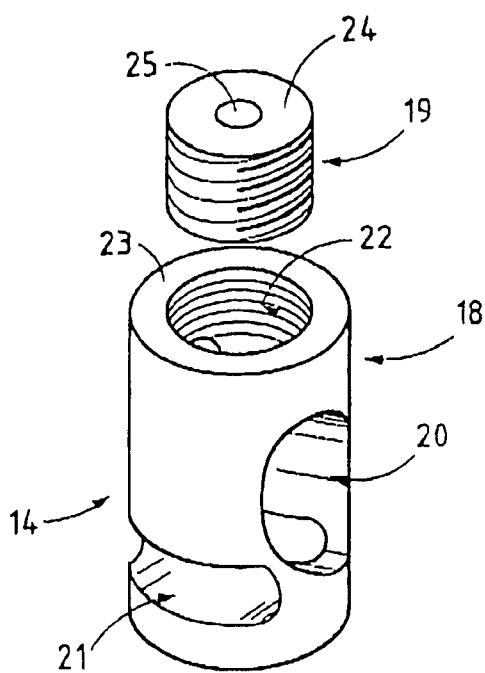
FIG. 4 is a diagrammatic perspective view of the locking piece and its set screw.

The connection device 1 includes a connection plate 10 as shown in FIG. 3. This plate 10 has two portions 11 and 12, the first portion 11 being designed to enable it to be connected to the pedicle screw 2 by means of the nut 8, and the second portion 12 being designed to enable it to be connected to the vertebral support rod 13 by means of a locking unit 14.

The first portion 11 of the connection plate presents a structure in the form of a crater in which a hole 15 is surrounded by two bearing faces, a concave bearing face 16 on top surrounding the hollow portion of the crater, and a convex face 17 underneath. The two bearing faces 16 and 17 have exactly the same curved configuration as the bases 6 and 9 of the head 4 on the pedicle screw 2, and of the nut 8. In addition, the inside diameter of the hole 15 in the connection plate 10 is greater than the outside diameter of the second threaded portion 7 of the pedicle screw 2. In one embodiment, where the second threaded portion 7 of the screw 2 is about 5 mm in diameter, the inside diameter of the hole 15 is about 7 mm.

The second portion 12 of the connection plate 10 extends the first portion 11; its section is substantially rectangular with rounded sides so as to avoid having sharp edges.

The locking element 14 is made up of a cylindrical locking piece 18 and a set screw 19. The cylindrical piece 18 has a first passage 20 passing through it diametrically for slidably receiving the vertebral support rod 13, and a second passage 21 passing through it diametrically and perpendicularly to the first passage 20 for the purpose of slidably receiving the second portion 12 of the connection plate 10. The two passages 20 and 21 are formed in such a manner that the inside volumes of the two passages intersect; this ensures that the vertebral support rod 13 comes into contact with the second portion 12 of the connection plate 10 when both elements are inserted in the locking piece 18.

The locking piece la has a third passage 22 formed in the circular face 23 of the cylindrical piece IS and opening out into the inside volume of the :first passage 20 remote from the'second passage 21.

The set screw 19 has a threaded periphery suitable for screw engagement in the third passage 22 which is correspondingly threaded., and a socket 25 is formed in the top plate 24 of the set.-screw 19 to receive a screw-driving tool.

The connection device 1 is put onto the segment of the spine for arthrodesis under the following conditions. The pedicle or joint screws 2 are initially implanted. Thereafter, a connection plate 10 is engaged on each screw 2 by inserting the second threaded portion of the screw 2 in the hole 15 of the plate 10 until the bottom seat face 17 comes to bear against the curved base 6 of the head 4 of the screw 2. A nut 8 is screwed loosely onto the second threaded portion 7 of each screw 2 so as to hold the corresponding connection plate 10 in place without locking it in position. A locking piece 14 is engaged on each connection piece 10 by causing the second portion 12 of said plate 10 to penetrate into the second passage 21 of the piece 18.

Thereafter, a vertebral support rod 13 is inserted successively into the first passage 20 of each of the adjacent locking pieces 18 along the segment of the spine.

Because of the connection via curved bearing faces 16, 17 of the connection piece 10 and via curved bases 6 on the heads 4 of the screws 2 and 9 of the nuts 8, and also because the locking pieces 18 can slide along the connection pieces 10, it is possible to provide internal mobility in translation and in rotation in all possible directions while assembling the instrumentation.

Prior to using the nuts 8 and-the set screw 19 for fixing together all of the elements of the device 1, the surgeon can thus ensure that all of these elements are in the desired relationship by bending the vertebral support rod 13 or by de-rotation thereof. These various operations, inserting and bending the rod 13, are made easier by the fact that the various connections are mobile.

Because of the spherical shape and the common centers of the bearing faces; 16. 17 and of the bases 6, 9, the various elements are clamped together via contact areas, thereby making the instrumentation very solid.

Because of the direct contact between the second portion 12 of the connection plate 10 and the vertebral support rod 13 where they pass through their respective passages 21 and 20, these two elements are both locked to the piece 16 by tightening only one set screw 19 in the passage 22.

To further restrict the overall size of this instrumentation, the second threaded portion 7 of the screw 2 is preferably suitable for being broken off at a height slightly above the nut 8 when the nut is in its locking position against the connection plate 10. This ability to break off can be obtained by weakening this portion of the rod via one or more notches so that it snaps cleanly when sufficient bending force is applied thereto by means of a suitable tool.

To reduce this size, the cylindrical locking piece 18 is preferably of an outside diameter which is substantially equal to the width of the first portion 11 of the connection plate 10. Under such circumstances, and as shown in FIG. 1, the second portion 12 of said plate 11 is of a width which is less than that of the first portion 11.

It can be advisable to prevent the cylindrical locking piece 18 from sliding freely once it has been put into place on the connection plate 10 and prior to being fixed thereto by means of the set screw 19. This can be achieved by any suitable means. In FIG. 1, by way of example, there is shown a screw 26 suitable for being screwed into-a tapped hole 27 formed in the end 28 of the second portion 12 of the-connection plate-lo. This screw 24 has a head 29 of-outside dimensions greater than those of said second portion 12. The screw 26 is put into place after the locking piece 16 has been engaged on the connection plate la, so that the head 29 of the screw 26 serves as an abutment and prevents the locking piece 18 from escaping from the connection plate 10.

The same abutment effect can be obtained by creating sufficient surface irregularity towards the end of the second portion 12 close to the end edge 28 of the connection plate 10 so as to impede free sliding of the locking piece 18. Such irregularity can be created by means of a tool of the pliers type suitable for locally deforming the material constituting the connection plate 10.

Figure 5:
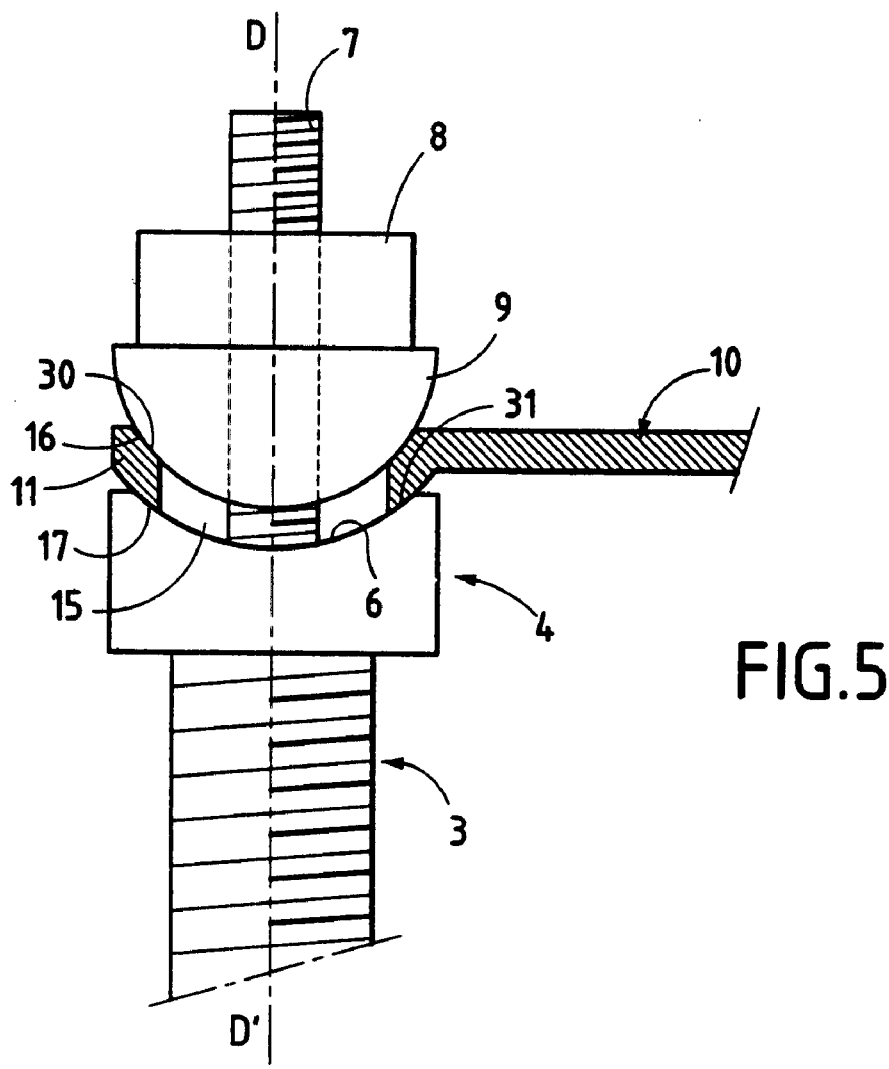
FIGS. 5 and 6 are diagrammatic longitudinal section views of the device through the connection between the pedicle screw, the connection plate, and the curved-base nut, shown in two different angular positions.
Figure 6:
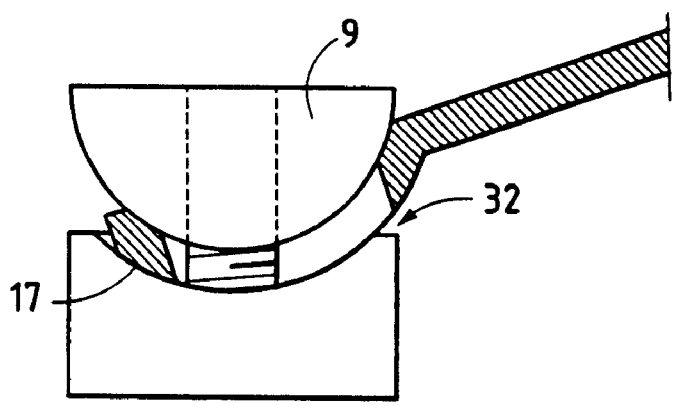

In order to understand how the connection plate 10 can move angularly in all directions relative to the pedicle screw 2, FIGS. 5 and 6 which are in longitudinal section show a portion of the connection plate 10, the nut 8 with its curved base 9, and the pedicle screw 2 with its two threaded portions 3, 7, its head 4, and its curved base 6. The various curves coincide in such a manner as to enable their surfaces to come into contact regardless of the relative displacement of the plate 10.

In FIG. 5, the hole 15 in the connection plate 10 is centered relative to the longitudinal axis DD' of the threaded portions 3 and 7 of the screw 2. Contact between the top bearing face 16 of the connection plate 10 and the curved base 9 of the nut 8 takes place im an annular zone 30 of a spherical surface about the axis DD'. Similarly, contact between the bottom bearing face 17 of the plate 10 and the curved base 6 of the head 4 of the screw 2 takes place in an annular spherical zone 31 about the axis DD'.

So long as the nut 8 is not tight against the plate 10, the plate can move in all possible directions between the two curved bases 6 and 9 of-the head 4 and the nut 8. This displacement is restricted solely by the size of the second threaded portion 7 of the nut and the size of the hole 15. As shown in FIG. 6, the second threaded portion 7 of the nut 2 constitutes an abutment for the plate 10, thereby limiting angular displacement thereof.

The dimensions of this second threaded portion 7 and of the hole 15 are designed in such a manner as to obtain the necessary angular displacements while the device 1 is being put into place.

As shown in FIG. 6, it should be observed that contact between the bottom bearing face 17 and the curved base 6 of the head 4 of the screw 2 is no longer circularly symmetrical. Specifically, there even exists a zone 32 where there is no longer any contact between these two elements. Nevertheless, this localized lack of engagement is compensated by greater contact area in other locations, thereby ensuring that once the nut a has been tightened, the instrumentation is very solid.

The present invention is not limited to the embodiment described above by way of non-exhaustive example. In particular, the base of the nut and the base of the head of the pedicle screw can be shaped oppositely from the example described and shown, there being a depression in the nut and a projection on the head of the screw.

What is claimed is:

1. An osteosynthesis connection device for a vertebral support rod, the device comprising:

a) a screw suitable for implanting in a spine, said screw comprising a bottom first threaded portion for implanting in the spine, a head having flats and a curved base, a top second threaded portion in line with the first threaded portion, and a locking nut suitable for co-operating with said second threaded portion and having a curved base, the screw having a central axis not lying in a same plane as a central axis of the vertebral support rod when implanted;

b) a connection piece having a bottom bearing face and a top bearing face, said connection piece having, for connection with the screw, a hole of an inside diameter greater than an outside diameter of said second threaded portion of the screw; and c) means for locking the vertebral support rod onto said connection piece, wherein said connection piece is locked in position on said screw once said locking nut has been tightened by said curved base of said locking nut bearing against said top bearing face of said connection piece, and by said bottom bearing face of said connection piece bearing against said curved base of said head of said screw; said curved surfaces of said bases of said head of said screw, of said locking nut, and of said top and bottom bearing faces of said connection piece being portions of spheres all having their centers in the same position, one of said top and bottom bearing faces being convex, and the other being concave, thereby enabling said connection piece to rotate relative to said screw.

2. The connection device according to claim 1, wherein said means for locking said connection piece on said vertebral support rod comprises:

a) a locking piece having a first passage for the vertebral support rod, a second passage for a portion of the connection piece, said first and second passages being substantially perpendicular and sharing a common inside volume in which said rod and said connection plate can come into contact, and a threaded third passage opening out into said inside volume of said first or second passage; and b) a set screw suitable for screw engagement in said third passage to lock said vertebral support rod and said connection piece in position by clamping said set screw, said rod, said connection piece, and said locking piece against one another.

3. The connection device according to claim 2, wherein the portion of said connection piece is designed to slide in said second passage of said locking piece and is a plate of substantially rectangular section with rounded sides, said second passage being shaped to enable said locking piece to slidably move and fit on said portion of said connection piece where the portion of the connection piece extends beyond said curved bearing faces.

4. The connection device according to claim 2, wherein said first passage for said vertebral support rod is of oblong cross-section, thereby allowing said support rod to move a little in a height direction prior to said set screw being tightened and enabling an already curved rod to be passed therethrough.

5. The connection device according to claim 2, wherein said locking piece is a cylindrical piece, said first and second passages extending along diametral directions that are perpendicular to each other, and said third passage being formed in one of the two circular faces of the cylinder and opening out into the inside volume of said first passage.

6. The connection device according to claim 2, wherein said connection piece has an abutment-forming element for said locking piece while the locking piece is free to slide, prior to said set screw being tightened.

7. The connection device according to claim 2, wherein the connection piece is constructed and arranged to form an abutment for said locking piece while the locking piece is free to slide, prior to said set screw being tightened.

8. The connection device according to claim 1, wherein said top second threaded portion of said screw is suitable for being broken off.

9. The connection device according to claim 8, wherein the second threaded portion is constructed and arranged to present a zone of weakness suitable for breaking.

* * * * *